United States Patent
Fulton et al.

(10) Patent No.: US 10,592,190 B2
(45) Date of Patent: Mar. 17, 2020

(54) METHOD AND APPARATUS FOR CONTROLLING THE OPERATION OF AN ELECTRONIC DEVICE

(71) Applicant: KONINKLIJKE PHILIPS N.V., Eindhoven (NL)

(72) Inventors: Paul Michael Fulton, Cambridge (GB); Laura Klaming, Amsterdam (NL); David Paul Walker, Cambridge (GB); Heribert Baldus, Aachen (DE); Dawid Ochal, Cambourne (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/738,708

(22) PCT Filed: Jun. 20, 2016

(86) PCT No.: PCT/EP2016/064151
§ 371 (c)(1),
(2) Date: Dec. 21, 2017

(87) PCT Pub. No.: WO2016/207101
PCT Pub. Date: Dec. 29, 2016

(65) Prior Publication Data
US 2018/0181356 A1 Jun. 28, 2018

(30) Foreign Application Priority Data
Jun. 25, 2015 (EP) .................................... 15173750

(51) Int. Cl.
*G06F 3/14* (2006.01)
*G06Q 10/10* (2012.01)
(Continued)

(52) U.S. Cl.
CPC ........... *G06F 3/1423* (2013.01); *G06Q 10/10* (2013.01); *G09B 7/00* (2013.01); *G09G 5/003* (2013.01);
(Continued)

(58) Field of Classification Search
CPC .... G06F 3/1423; G06F 1/1647; G06F 1/1649; G06F 1/165; G16H 40/63; G06Q 10/10;
(Continued)

(56) References Cited

U.S. PATENT DOCUMENTS 8,786,581 B2 * 7/2014 Ishii .................... G06F 1/1616
345/204
8,868,135 B2 * 10/2014 Sirpal .................. G06F 3/1438
455/566
(Continued)

FOREIGN PATENT DOCUMENTS

EP 2632189 8/2013

OTHER PUBLICATIONS

"Philips Motiva Mobile-Empowering Patients"; 2013 Koninklijke Philips N.V., 2 Page Document.
(Continued)

*Primary Examiner* — Tom V Sheng

(57) ABSTRACT

There is provided a method of controlling the operation of a first electronic device having a first display screen, the method comprising obtaining (101; 111) measurements of a position of the first electronic device relative to a second electronic device, an orientation of the first display screen, and/or an orientation of a second display screen of a second electronic device; determining (103; 113), using the obtained measurements, one or both of (i) whether a first user using the first electronic device can view the second display screen, and (ii) whether a second user using the second electronic device can view the first display screen;
(Continued)

and controlling (105; 115) the display of information on the first display screen based on the result of the step of determining.

22 Claims, 8 Drawing Sheets

(51) Int. Cl.
*G09B 7/00* (2006.01)
*G16H 40/63* (2018.01)
*G09G 5/00* (2006.01)
*G06Q 50/22* (2018.01)

(52) U.S. Cl.
CPC ............ *G16H 40/63* (2018.01); *G06Q 50/22* (2013.01); *G09G 2354/00* (2013.01); *G09G 2358/00* (2013.01)

(58) Field of Classification Search
CPC .......... G06Q 50/22; G09B 7/00; G09G 5/003; G09G 2354/00; G09G 2356/00; G09G 2358/00
See application file for complete search history.

(56) References Cited

U.S. PATENT DOCUMENTS

| | | | | |
|---|---|---|---|---|
| 9,690,533 | B2* | 6/2017 | Ohta | G06F 3/1423 |
| 9,880,800 | B1* | 1/2018 | Knepper | G06F 3/1446 |
| 2006/0082518 | A1* | 4/2006 | Ram | G06F 1/1601 |
| | | | | 345/1.1 |
| 2007/0078965 | A1 | 4/2007 | Shimamura et al. | |
| 2009/0239591 | A1 | 9/2009 | Alameh et al. | |
| 2010/0245106 | A1* | 9/2010 | Miller | G06F 1/1618 |
| | | | | 340/686.1 |
| 2011/0060715 | A1 | 3/2011 | Shankle | |
| 2011/0216064 | A1* | 9/2011 | Dahl | G06F 1/1616 |
| | | | | 345/428 |
| 2011/0225538 | A1* | 9/2011 | Oyagi | G06F 1/1692 |
| | | | | 715/781 |
| 2012/0014558 | A1 | 1/2012 | Stafford et al. | |
| 2012/0040719 | A1* | 2/2012 | Lee | G06F 1/1626 |
| | | | | 455/557 |
| 2012/0081271 | A1* | 4/2012 | Gimpl | G06F 1/1616 |
| | | | | 345/1.3 |
| 2012/0081277 | A1* | 4/2012 | de Paz | G06F 1/1616 |
| | | | | 345/156 |
| 2012/0023883 | A1 | 9/2012 | Benford | |
| 2012/0238831 | A1 | 9/2012 | Benford | |
| 2012/0240055 | A1* | 9/2012 | Webber | G06Q 10/107 |
| | | | | 715/752 |
| 2012/0280924 | A1* | 11/2012 | Kummer | H04M 1/0235 |
| | | | | 345/501 |
| 2013/0113628 | A1 | 5/2013 | Shepherd et al. | |
| 2013/0169545 | A1* | 7/2013 | Eaton | H04M 1/0241 |
| | | | | 345/173 |
| 2013/0241954 | A1* | 9/2013 | Yu | G06F 3/1446 |
| | | | | 345/629 |
| 2013/0288603 | A1* | 10/2013 | Iwasaki | H04W 4/38 |
| | | | | 455/41.2 |
| 2013/0328934 | A1* | 12/2013 | Lim | G06F 1/1616 |
| | | | | 345/650 |
| 2014/0002327 | A1* | 1/2014 | Toren | G06F 3/1423 |
| | | | | 345/1.1 |
| 2014/0184628 | A1* | 7/2014 | Lee | G06F 3/1423 |
| | | | | 345/545 |
| 2014/0206288 | A1 | 7/2014 | Liu et al. | |
| 2015/0035998 | A1* | 2/2015 | Mathew | H04N 5/2258 |
| | | | | 348/207.1 |
| 2015/0116362 | A1* | 4/2015 | Aurongzeb | H04N 7/15 |
| | | | | 345/650 |
| 2015/0116364 | A1* | 4/2015 | Aurongzeb | G06F 3/0487 |
| | | | | 345/659 |
| 2015/0130725 | A1* | 5/2015 | Knepper | G06F 1/1643 |
| | | | | 345/173 |

OTHER PUBLICATIONS

Alshurafa N. et al, Anti-Cheating: Detecting Self-Inflicted and Impersonator Cheaters for Remote Health Monitoring Systems with Wearable Sensors, BSN '14 Proceedings of the 2014 11th International Conference on Wearable and Implantable Body Sensor Networks, pp. 92-97.

* cited by examiner

METHOD AND APPARATUS FOR CONTROLLING THE OPERATION OF AN ELECTRONIC DEVICE

CROSS-REFERENCE TO PRIOR APPLICATIONS

This application is the U.S. National Phase application under 35 U.S.C. § 371 of International Application No. PCT/EP2016/064151, filed on Jun. 20, 2016, which claims the benefit of European Patent Application No. 15173750.9, filed on Jun. 25, 2015. These applications are hereby incorporated by reference in their entirety herein.

TECHNICAL FIELD

The invention relates to a method and apparatus for controlling the operation of an electronic device, for example an electronic device that is used by a user that is performing an assessment or test, or being used to play a game.

BACKGROUND TO THE INVENTION

Collecting data from patients or users by means of formalized assessments or tests is an important process for clinicians, particularly for conditions involving cognitive decline or mental health issues. Tests are traditionally provided as paper forms, either for completion individually or through one person performing a test on another. Computerizing tests can provide advantages such as speeding up the workflow, allowing automatic collection of data, adding interactive elements, dynamically changing the questions or just making the test presentation more engaging to users. Various examples of computerized tests are known in the art. For example, a test may be run by doctors on a tablet computer to assess a patient sitting alongside them for indicators of dementia.

A further advantage of computerized tests is that they may be provided remotely to people at home using a tablet or mobile device. The Motiva Mobile system from Philips is designed to provide a range of services to patients at home, for instance via a tablet. With one service the user is presented with multiple-choice questionnaires on a range of health subjects.

In the case of a person with cognitive impairment or dementia, an informal career (or perhaps a community nurse) may be responsible for supervising the test. In such a test, the patient may be provided with an electronic device on which the test content is to be displayed and the career or assessor may be provided with an electronic device that they can use to control the test (e.g. by initiating the start of the test, providing specified guidance for the test (i.e. reading out instructions to the patient), etc.). The test content can include questions, reaction tests, memory tests, etc., and the result of the test can provide an indication of the patient's medical condition.

SUMMARY OF THE INVENTION

In this type of assessment or test it may be important that the assessor does not interfere with the assessment by, for example, helping the patient with certain questions or tasks (e.g. by reading the content provided to the patient by the patient's electronic device or giving the patient the answer to a question), and as such the assessor should not be able to view the information provided to the patient by their electronic device. Alternatively or in addition, it may be important that the patient does not view the information provided to the assessor by their electronic device, since this may contain information that the patient can use to unfair advantage (e.g. hints for completing the current task).

The invention aims to improve the reliability of this type of assessment by reducing the risk of cheating by the patient or collaboration between the patient and assessor by changing the information displayed on a display screen of one of the electronic devices if it is possible that a user of one of the electronic devices involved in the assessment can see the display screen of the other electronic device.

In addition to its use in electronic devices used for administering tests or assessments (such as cognitive assessments as described herein), it will be appreciated that the invention can be used in electronic devices for playing games where it is important for a player or players to conceal information from the other player or players (e.g. in an electronic card game where each player's hand of cards is displayed on their electronic device).

Therefore, in accordance with a first aspect of the invention, there is provided a method of controlling the operation of a first electronic device having a first display screen, the method comprising obtaining measurements of an orientation of a second display screen of a second electronic device, and one or both of a position of the first electronic device relative to the second electronic device and an orientation of the first display screen; determining, using the obtained measurements, whether a first user using the first electronic device can view the second display screen; and controlling the display of information on the first display screen based on the result of the step of determining. Thus, the claimed invention provides that the information displayed on the first display screen depends on whether either user can view the display screen of the other electronic device, which means that, in the case of an assessment or test, the display of information to the first user can be controlled in order to reduce the chance of cheating or collaboration between the users that might affect the reliability of the result of the assessment.

In some embodiments, the step of controlling the display of information on the first display screen comprises changing the information displayed on the first display screen if it is determined that the first user can view the second display screen.

In alternative embodiments, the step of controlling the display of information on the first display screen comprises causing the presentation of first information using the first display screen if it is determined that the first user cannot view the second display screen; and causing the presentation of second information using the first display screen if it is determined that the first user can view the second display screen.

In alternative embodiments, the step of controlling the display of information on the first display screen comprises allowing the display of information on the first display screen if it is determined that the first user cannot view the second display screen; and stopping or preventing the display of information on the first display screen if it is determined that the first user can view the second display screen.

The above three embodiments provide alternative ways of controlling the display of information so that a user of one device cannot view the information displayed on the other device.

In some embodiments, the step of determining comprises using the orientation of the first display screen and/or position of the first electronic device relative to the second electronic device to estimate a position of the first user when using the first electronic device; and using the orientation of the second display screen, the position of the first electronic device relative to a second electronic device and the estimated position of the first user to determine if the first user can view the second display screen.

In some embodiments, the measurements are obtained using one or more of an accelerometer in the first electronic device, an accelerometer in the second electronic device, a magnetometer in the first electronic device, a magnetometer in the second electronic device, a gyroscope in the first electronic device, a gyroscope in the second electronic device, and one or more cameras.

In some embodiments, an initial set of measurements are obtained when the first electronic device and the second electronic device are in an arrangement in which the first user cannot view the second display screen; and wherein the step of determining comprises determining that the first user can view the second display screen if the orientation of the first display screen and/or the orientation of the second display screen change from the initial set of measurements by more than a threshold amount. This embodiment has the advantage of simplifying the processing required to determine if the first user can view the second display screen and/or if the second user can view the first display screen.

In some embodiments the method further comprises determining if the first electronic device is being held or used by a user; wherein the step of controlling further comprises controlling the display of information on the first display screen based on whether the first electronic device is being held or used by a user. This embodiment has the advantage that cheating by the first user or collaboration between the users in which the first user puts down their electronic device (in the correct orientation so that information continues to be displayed on the display screen of the first electronic device) and the first user moves to a position in which they can view the display screen of the second electronic device is prevented.

In some embodiments, the method further comprises determining if the second electronic device is being held or used by a user; wherein the step of controlling further comprises controlling the display of information on the first display screen based on whether the second electronic device is being held or used by a user. This embodiment has the advantage that cheating by the second user or collaboration between the users in which the second user puts down their electronic device (in the correct orientation so that information continues to be displayed on the display screen of the first electronic device) and the second user moves to a position in which they can view the display screen of the first electronic device is prevented.

In some embodiments, the method further comprises using a camera to determine if a user is using or holding the first electronic device; wherein the step of controlling further comprises controlling the display of information on the first display screen based on whether a user is using or holding the first electronic device. This embodiment has the advantage that cheating by the first user or collaboration between the users in which the first user puts down their electronic device (in the correct orientation so that information continues to be displayed on the display screen of the first electronic device) and the first user moves to a position in which they can view the display screen of the second electronic device is prevented.

In some embodiments, the method further comprises using a camera to determine if a user is using or holding the second electronic device; wherein the step of controlling further comprises controlling the display of information on the first display screen based on whether a user is using or holding the second electronic device. This embodiment has the advantage that cheating by the second user or collaboration between the users in which the second user puts down their electronic device (in the correct orientation so that information continues to be displayed on the display screen of the first electronic device) and the second user moves to a position in which they can view the display screen of the first electronic device is prevented.

In some embodiments, the method is performed in the first electronic device. In other embodiments, the method is performed in the second electronic device or another electronic device, and the step of controlling comprises sending a signal to the first electronic device to control the display of information on the first display screen.

According to a second aspect, there is provided a method of controlling the operation of a first electronic device having a first display screen and a second electronic device having a second display screen, the method comprising controlling the operation of the first electronic device according to any of the method embodiments described above; and controlling the display of information on the second display screen based on whether the first user can view the second display screen. This aspect has the advantage that both users can be prevented from viewing information displayed on the display screen of the other electronic device.

Further embodiments of the second aspect are contemplated in which the display of information on the second display screen is controlled in a similar way to the display of information on the first display screen described above.

According to a third aspect, there is provided a method of controlling the operation of a first electronic device having a first display screen, the method comprising obtaining measurements of an orientation of the first display screen, and one or both of a position of the first electronic device relative to a second electronic device and an orientation of a second display screen of the second electronic device; determining, using the obtained measurements, whether a second user using the second electronic device can view the first display screen; and controlling the display of information on the first display screen based on the result of the step of determining.

In some embodiments, the step of controlling the display of information on the first display screen comprises changing the information displayed on the first display screen if it is determined that the second user can view the first display screen.

In some embodiments, the step of controlling the display of information on the first display screen comprises causing the presentation of first information using the first display screen if it is determined that the second user cannot view the first display screen; and causing the presentation of second information using the first display screen if it is determined that the second user can view the first display screen.

In some embodiments, the step of controlling the display of information on the first display screen comprises allowing the display of information on the first display screen if it is determined that the second user cannot view the first display screen; and stopping or preventing the display of information on the first display screen if it is determined that the second user can view the first display screen.

In some embodiments, the step of determining comprises using the orientation of the second display screen and/or position of the first electronic device relative to the second electronic device to estimate a position of the second user when using the second electronic device; and using the orientation of the first display screen, the position of the first electronic device relative to a second electronic device, and the estimated position of the second user to determine if the second user can view the first display screen.

In some embodiments, the measurements are obtained using one or more of an accelerometer in the first electronic device, an accelerometer in the second electronic device, a magnetometer in the first electronic device, a magnetometer in the second electronic device, a gyroscope in the first electronic device, a gyroscope in the second electronic device, and one or more cameras.

In some embodiments, an initial set of measurements are obtained when the first electronic device and the second electronic device are in an arrangement in which the second user cannot view the first display screen; and wherein the step of determining comprises determining that the second user can view the first display screen if the orientation of the first display screen and/or the orientation of the second display screen change from the initial set of measurements by more than a threshold amount.

In some embodiments, the method further comprises determining if the first electronic device is being held or used by a user; wherein the step of controlling further comprises controlling the display of information on the first display screen based on whether the first electronic device is being held or used by a user.

In some embodiments, the method further comprises determining if the second electronic device is being held or used by a user; wherein the step of controlling further comprises controlling the display of information on the first display screen based on whether the second electronic device is being held or used by a user.

According to a fourth aspect, there is provided a method of controlling the operation of a first electronic device having a first display screen and a second electronic device having a second display screen, the method comprising controlling the operation of the first electronic device according to the methods described above; and controlling the display of information on the second display screen based on whether the second user can view the first display screen.

According to a fifth aspect, there is provided a computer program product comprising a computer readable medium having computer readable code embodied therein, the computer readable code being configured such that, on execution by a suitable computer or processor, the computer or processor is caused to perform any of the methods described above.

According to a sixth aspect, there is provided an apparatus, for controlling the operation of a first electronic device having a first display screen, the apparatus comprising a processing unit that is configured to obtain measurements of an orientation of a second display screen of a second electronic device, and one or both of a position of the first electronic device relative to the second electronic device and an orientation of the first display screen; determine, using the obtained measurements, whether a first user using the first electronic device can view the second display screen; and control the display of information on the first display screen based on whether the first user can view the second display screen.

In some embodiments, the processing unit is configured to control the display of information on the first display screen by changing the information displayed on the first display screen if it is determined that the first user can view the second display screen.

In alternative embodiments, the processing unit is configured to control the display of information on the first display screen by causing the presentation of first information using the first display screen if it is determined that the first user cannot view the second display screen; and causing the presentation of second information using the first display screen if it is determined that the first user can view the second display screen.

In alternative embodiments, the processing unit is configured to control the display of information on the first display screen by allowing the display of information on the first display screen if it is determined that the first user cannot view the second display screen; and stopping or preventing the display of information on the first display screen if it is determined that the first user can view the second display screen.

The above three embodiments provide alternative ways of controlling the display of information so that a user of one device cannot view the information displayed on the other device.

In some embodiments, the processing unit is configured to determine whether a first user using the first electronic device can view a second display screen of the second electronic device by using the orientation of the first display screen and/or position of the first electronic device relative to the second electronic device to estimate a position of the first user when using the first electronic device; and using the orientation of the second display screen, the position of the first electronic device relative to a second electronic device and the estimated position of the first user to determine if the first user can view the second display screen.

In some embodiments, the measurements are obtained using one or more of an accelerometer in the first electronic device, an accelerometer in the second electronic device, a magnetometer in the first electronic device, a magnetometer in the second electronic device, a gyroscope in the first electronic device, a gyroscope in the second electronic device, and one or more cameras.

In some embodiments, the processing unit is configured to obtain an initial set of measurements when the first electronic device and the second electronic device are in an arrangement in which the first user cannot view the second display screen; and wherein the processing unit is configured to determine that the first user can view the second display screen if the orientation of the first display screen and/or the orientation of the second display screen change from the initial set of measurements by more than a threshold amount. This embodiment has the advantage of simplifying the processing required to determine if the first user can view the second display screen.

In some embodiments the processing unit is further configured to determine if the first electronic device is being held or used by a user; wherein the processing unit is configured to control the display of information on the first display screen based on whether the first electronic device is being held or used by a user. This embodiment has the advantage that cheating by the first user or collaboration between the users in which the first user puts down their electronic device (in the correct orientation so that information continues to be displayed on the display screen of the first electronic device) and the first user moves to a position in which they can view the display screen of the second electronic device is prevented.

In some embodiments, the processing unit is further configured to determine if the second electronic device is being held or used by a user; wherein the processing unit is configured to control the display of information on the first display screen based on whether the second electronic device is being held or used by a user. This embodiment has the advantage that cheating by the second user or collaboration between the users in which the second user puts down their electronic device (in the correct orientation so that information continues to be displayed on the display screen of the first electronic device) and the second user moves to a position in which they can view the display screen of the first electronic device is prevented.

In some embodiments, the processing unit is further configured to use a camera to determine if a user is using or holding the first electronic device; wherein the processing unit is configured to control the display of information on the first display screen based on whether a user is using or holding the first electronic device. This embodiment has the advantage that cheating by the first user or collaboration between the users in which the first user puts down their electronic device (in the correct orientation so that information continues to be displayed on the display screen of the first electronic device) and the first user moves to a position in which they can view the display screen of the second electronic device is prevented.

In some embodiments, the processing unit is further configured to use a camera to determine if a user is using or holding the second electronic device; wherein the processing unit is configured to control the display of information on the first display screen based on whether a user is using or holding the second electronic device. This embodiment has the advantage that cheating by the second user or collaboration between the users in which the second user puts down their electronic device (in the correct orientation so that information continues to be displayed on the display screen of the first electronic device) and the second user moves to a position in which they can view the display screen of the first electronic device is prevented.

In some embodiments, the apparatus is the first electronic device. In other embodiments, the apparatus is the second electronic device or another electronic device, and the processing unit is configured to control the display of information by the first display screen by triggering or causing the sending of a control signal to the first electronic device.

According to a seventh aspect, there is provided an apparatus, for controlling the operation of a first electronic device having a first display screen, the apparatus comprising a processing unit that is configured to obtain measurements of an orientation of the first display screen, and one or both of a position of the first electronic device relative to a second electronic device, and an orientation of a second display screen of the second electronic device; determine, using the obtained measurements, whether a second user using the second electronic device can view the first display screen; and control the display of information on the first display screen based on whether the second user can view the first display screen.

In some embodiments, the processing unit is configured to control the display of information on the first display screen by changing the information displayed on the first display screen if it is determined that the second user can view the first display screen.

In alternative embodiments, the processing unit is configured to control the display of information on the first display screen by causing the presentation of first information using the first display screen if it is determined that the second user cannot view the first display screen; and causing the presentation of second information using the first display screen if it is determined that the second user can view the first display screen.

In alternative embodiments, the processing unit is configured to control the display of information on the first display screen by allowing the display of information on the first display screen if it is determined that the second user cannot view the first display screen; and stopping or preventing the display of information on the first display screen if it is determined that the second user can view the first display screen.

The above three embodiments provide alternative ways of controlling the display of information so that a user of one device cannot view the information displayed on the other device.

In some embodiments, the processing unit is configured to determine whether a second user using the second electronic device can view the first display screen by using the orientation of the second display screen and/or position of the first electronic device relative to the second electronic device to estimate a position of the second user when using the second electronic device; and using the orientation of the first display screen, the position of the first electronic device relative to a second electronic device, and the estimated position of the second user to determine if the second user can view the first display screen.

In some embodiments, the measurements are obtained using one or more of an accelerometer in the first electronic device, an accelerometer in the second electronic device, a magnetometer in the first electronic device, a magnetometer in the second electronic device, a gyroscope in the first electronic device, a gyroscope in the second electronic device, and one or more cameras.

In some embodiments, the processing unit is configured to obtain an initial set of measurements when the first electronic device and the second electronic device are in an arrangement in which the second user cannot view the first display screen; and the processing unit is configured to determine that the second user can view the first display screen if the orientation of the first display screen and/or the orientation of the second display screen change from the initial set of measurements by more than a threshold amount. This embodiment has the advantage of simplifying the processing required to determine if the second user can view the first display screen.

In some embodiments the processing unit is further configured to determine if the first electronic device is being held or used by a user; wherein the processing unit is configured to control the display of information on the first display screen based on whether the first electronic device is being held or used by a user. This embodiment has the advantage that cheating by the first user or collaboration between the users in which the first user puts down their electronic device (in the correct orientation so that information continues to be displayed on the display screen of the first electronic device) and the first user moves to a position in which they can view the display screen of the second electronic device is prevented.

In some embodiments, the processing unit is further configured to determine if the second electronic device is being held or used by a user; wherein the processing unit is configured to control the display of information on the first display screen based on whether the second electronic device is being held or used by a user. This embodiment has the advantage that cheating by the second user or collaboration between the users in which the second user puts down their electronic device (in the correct orientation so that information continues to be displayed on the display screen of the first electronic device) and the second user moves to a position in which they can view the display screen of the first electronic device is prevented.

In some embodiments, the processing unit is further configured to use a camera to determine if a user is using or holding the first electronic device; wherein the processing unit is configured to control the display of information on the first display screen based on whether a user is using or holding the first electronic device. This embodiment has the advantage that cheating by the first user or collaboration between the users in which the first user puts down their electronic device (in the correct orientation so that information continues to be displayed on the display screen of the first electronic device) and the first user moves to a position in which they can view the display screen of the second electronic device is prevented.

In some embodiments, the processing unit is further configured to use a camera to determine if a user is using or holding the second electronic device; wherein the processing unit is configured to control the display of information on the first display screen based on whether a user is using or holding the second electronic device. This embodiment has the advantage that cheating by the second user or collaboration between the users in which the second user puts down their electronic device (in the correct orientation so that information continues to be displayed on the display screen of the first electronic device) and the second user moves to a position in which they can view the display screen of the first electronic device is prevented.

In some embodiments, the apparatus is the first electronic device. In other embodiments, the apparatus is the second electronic device or another electronic device, and the processing unit is configured to control the display of information by the first display screen by triggering or causing the sending of a control signal to the first electronic device.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
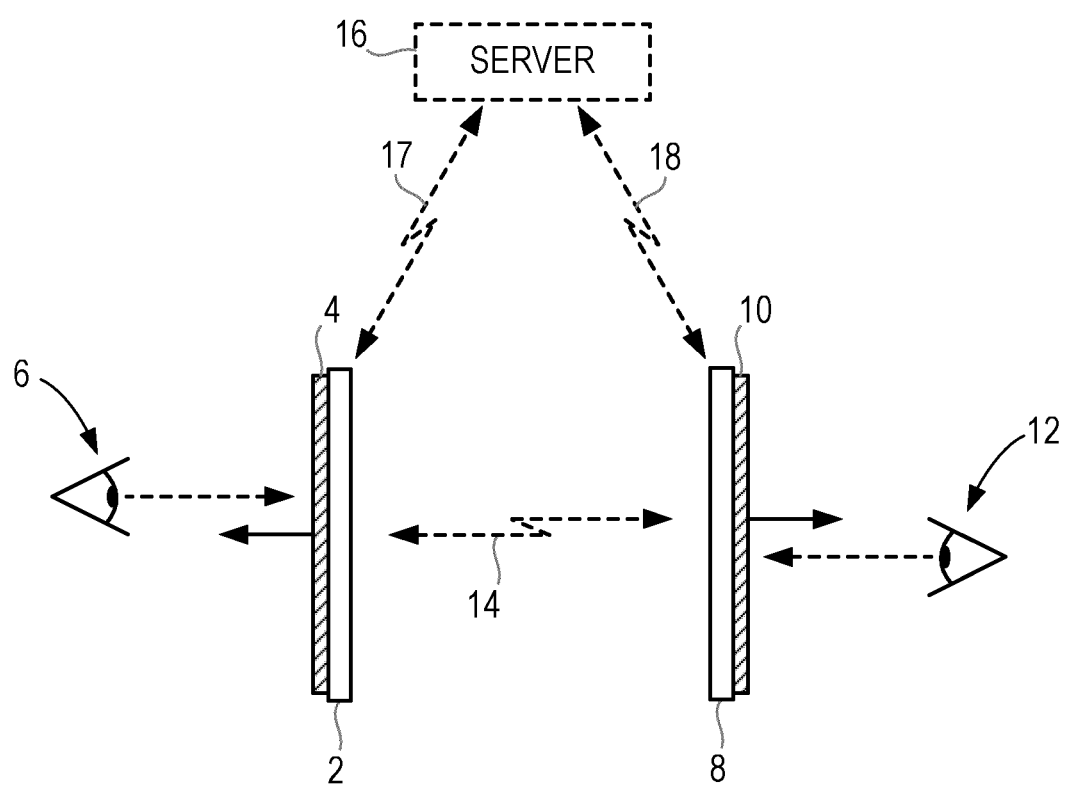
FIG. 1 is an illustration of a first electronic device and a second electronic device according to the invention.

FIG. 1 represents a side view of two electronic devices being used by respective users. A first electronic device 2 that has a first display screen 4 is being used by a first user 6 and a second electronic device 8 that has a second display screen 10 is being used by a second user 12.

The electronic devices 2, 8 may be any type of electronic device that has a display screen for displaying information to a user of the electronic device. Each electronic device can be, for example, a mobile telephone, a smart phone, a tablet, a personal digital assistant, a home computer, or a set-top box for a television or monitor. The electronic devices 2, 8 may the same type of device, or different types of devices. One or both of the electronic devices 2, 8 may be conventional off-the-shelf devices that are running an application or other software program to enable the device to operate according to embodiments of the invention described herein.

In some embodiments the electronic devices 2, 8 can communicate with each other, either directly (for example via a wireless connection, such as Wi-Fi, Bluetooth, Near Field Communication (NFC), etc. or a wired connection, such as Ethernet or USB) as indicated by arrow 14, or via another electronic device, such as a remote server 16, as indicated by arrows 17, 18. In other embodiments, the electronic devices 2, 8 may not communicate with each other, but instead communicate with the other electronic device 16.

In some embodiments, the electronic devices 2, 8 may be used for administering a test or assessment to a user of one of the devices. For example, the first user 6 may be a patient that is required to complete a test to assess their cognitive impairment. The second user 12 may manage, control or run the test using the second electronic device 8.

In alternative embodiments, the electronic devices 2, 8 can be used to play a game in which one or both display screens are used to present information to the respective users of the electronic devices that is to be hidden or kept secret from the other user. For example each electronic device 2, 8 can be used as part of an electronic card game in which each player's (user's) hand of cards is displayed on their electronic device.

Those skilled in the art will appreciate that the invention described herein can be put to uses other than cognitive or other health-based assessments or playing games. For example, other uses may include improving or ensuring privacy of user information that is displayed on a display screen of the user's electronic device.

As noted below, in some embodiments the invention can be implemented in one or both of the electronic devices 2, 8. However, in other embodiments, the invention can be implemented in another device (e.g. server 16).

Figure 2:
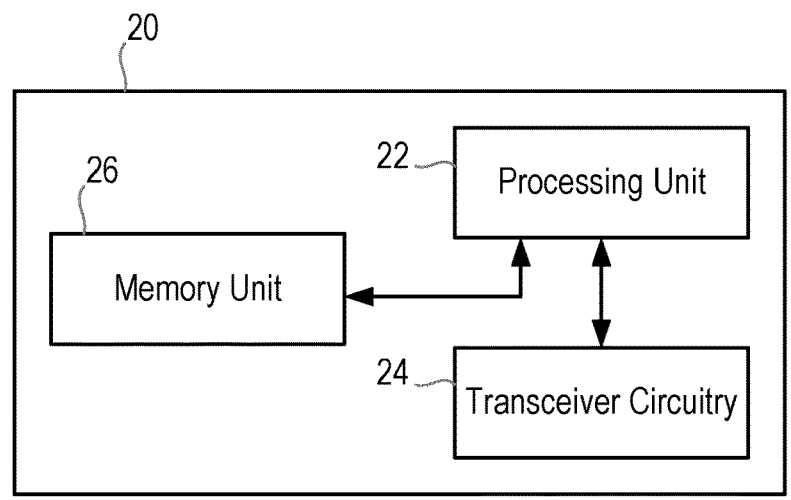
FIG. 2 is a block diagram of an apparatus according to an embodiment.

FIG. 2 is a block diagram of a general apparatus 20 that can be used to implement the invention. In some embodiments the apparatus 20 can be, or be part of, an electronic device 2, 8 (as described below with reference to FIG. 3), but in other embodiments the apparatus 20 can be, or be part of, another electronic device (e.g. server 16).

The apparatus 20 comprises a processing unit 22 that controls the operation of the apparatus 20 and that can perform a method of controlling the operation of an electronic device as described below. The apparatus 20 also comprises transceiver circuitry 24 that is connected to the processing unit 22 that enables the apparatus 20 to transmit information and/or signals to, and/or receive information and/or signals from, other electronic devices, such as electronic devices 2, 8 and server 16. The apparatus 20 also comprises a memory unit 26 that is connected to the processing unit 22. The memory unit 26 can be used to store computer readable program code that can be executed by the processing unit 22 to perform the method according to the invention.

The processing unit 22 can be or comprise one or more processors, multi-core processors or processing modules for implementing the method described herein. In some embodiments, the processing unit 22 can be implemented as a plurality of processing sub-units or modules, with each module being configured to perform a particular part or step of the method described herein. In some embodiments the processing unit 22 can be dedicated to the purpose of performing the method described herein, but in other embodiments the processing unit 22 can be a general-purpose processing unit 22 that can execute suitable software or firmware to enable the apparatus 20 to perform the method described herein.

The memory unit 26 can be any suitable electronic component that can be used to store information or program code for use by the apparatus 20. For example the memory unit 26 can be a fixed or removable hard disk, solid-state storage device or optical storage device.

The transceiver circuitry 24 can be circuitry that enables the apparatus 20 to communicate with other devices in a wired and/or wireless manner (for example using a short-range wireless communication standard such as Near Field Communication (NFC), Bluetooth or Wi-Fi, or a cellular communication standard such as GSM (Global Standard for Mobile Communications), LTE (Long Term Evolution), etc.).

It will be appreciated that in practical implementations, the apparatus 20 may comprise further components to those shown in FIG. 2, such as a power supply (or means for connecting the apparatus 20 to a power supply), and/or a user interface (such as one or more buttons or keys, switches, dials or a touch screen) to allow a user to control the operation of the apparatus 20.

Figure 3:
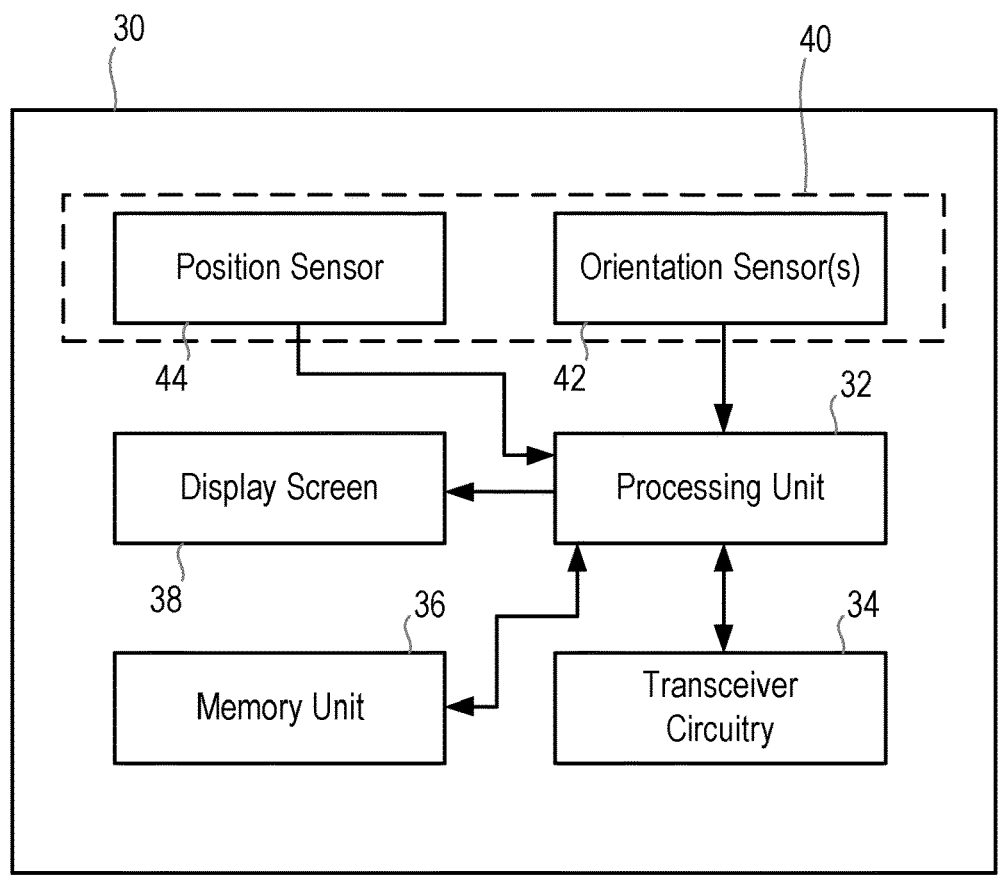
FIG. 3 is a block diagram of an electronic device according to an embodiment.

FIG. 3 is a block diagram illustrating components of an exemplary electronic device 2, 8 that can be used in the embodiments described herein.

The electronic device 30 comprises a processing unit 32 that controls the operation of the electronic device 30 and that can perform, or be used in, the method of controlling the operation of an electronic device as described below. The electronic device 30 also comprises transceiver circuitry 34 that is connected to the processing unit 32 that enables the electronic device 30 to transmit information and/or signals to, and/or receive information and/or signals from, other electronic devices, such as electronic devices 2, 8, apparatus 20. The electronic device 30 also comprises a memory unit 36 that is connected to the processing unit 32. The memory unit 36 can be used to store computer readable program code that can be executed by the processing unit 32 to perform the method according to the invention.

Processing unit 32, transceiver circuitry 34 and memory unit 36 are generally as described above for processing unit 22, transceiver circuitry 24 and memory unit 26 in apparatus 20.

The electronic device 30 also comprises a display screen 38 that is connected to the processing unit 32 and that is used to display information to the user of the electronic device 30 based on control signals from the processing unit 32. In some embodiments the display screen 30 is a touch screen. The side of the electronic device 30 on which the display screen 38 is located is referred to herein as the front side or front face of the electronic device 30. The side of the electronic device 30 that is opposite the front side or front face of the electronic device 30 is referred to herein as the back side or back face of the electronic device 30.

The electronic device 30 also comprises one or more sensors 40 that can be used to provide measurements of the orientation and/or position of the electronic device 30. These measurements are processed so that the direction in which the display screen 38 is facing can be determined or estimated.

In some embodiments the one or more sensors 40 can comprise one or more orientation sensors 42 that measure the orientation of the electronic device 30 in three dimensions. Suitable sensors include an accelerometer that measures accelerations in three dimensions (or three accelerometers that each measure acceleration along a respective axis), a magnetometer (for measuring the strength and direction of the Earth's magnetic field) and a gyroscope. The electronic device 30 may comprise any one or a combination of these exemplary types of sensors 42.

In some embodiments, the one or more sensors 40 can comprise a sensor 44 for measuring the position of the electronic device 30 (this position sensor 44 can be in addition or alternatively to the one or more orientation sensors 42). In some embodiments, the position sensor 44 can be a sensor that measures the absolute position of the electronic device 30 (i.e. absolute in the sense that it is measured with reference to an external reference frame), such as a satellite positioning system (SPS) receiver or a sensor that measures the absolute position using triangulation (e.g. triangulation of signals from different base station transmitters in a communication network). In other embodiments, the position sensor 44 can be a sensor that measures the position of the electronic device 30 relative to another electronic device 30. This may be measured in terms of a distance between the electronic devices 30 (for example using the time-of-flight of a signal or signals between the devices)—in which case the transceiver circuitry 34 can be used for this purpose (which can avoid the need for a separate sensor 44) and/or the direction from one electronic device to the other (e.g. the electronic device 30 is due north of the other device).

In further embodiments, which are described in more detail below, the electronic device 30 may include one or more cameras which can be used to determine if a user is in front of the display screen 38 of the electronic device 30. The one or more cameras may be located on the front face and/or back face of the electronic device 30.

It will be appreciated that in practical implementations, the electronic device 30 may comprise further components to those shown in FIG. 3, such as a power supply (or means for connecting the electronic device 30 to a power supply), a or further user interface components (such as one or more buttons or keys, switches, dials, etc.) to allow a user to control the operation of the electronic device 30, and one or more speakers for providing audible output from the electronic device 30.

Figure 4:
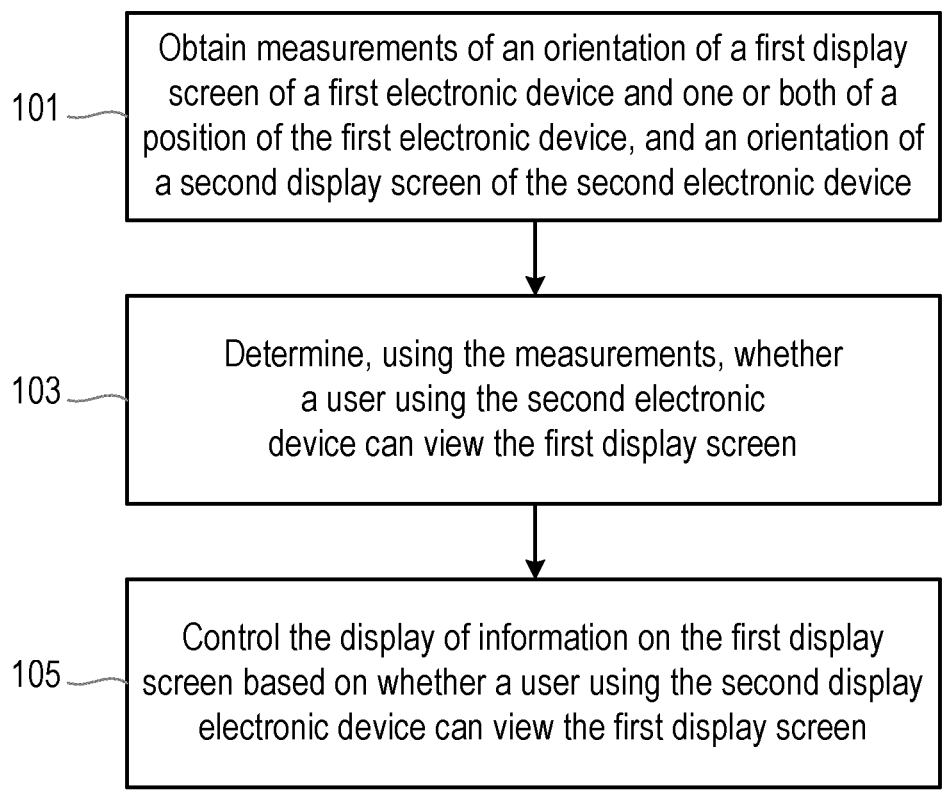
FIG. 4 is a flow chart illustrating a method according to a first embodiment.

The flow chart in FIG. 4 illustrates a method of operating a first electronic device 2 according to an embodiment of the invention. In this embodiment, the display of information on a display screen 4 of the first electronic device 2 (which is referred to as the first display screen 4) is controlled based on whether a user of a second electronic device 8 can view the first display screen 4. It will be appreciated that it is not necessary to determine whether the user of the second electronic device 8 is also viewing the display screen 10 of the second electronic device 8, although in some embodiments this is determined.

In a first step, step 101, measurements of a position of the first electronic device 2 relative to the second electronic device 8 and an orientation of the first display screen 4 are obtained. The position can be measured using a sensor or sensors 40, 44 in one or both of the first and second electronic devices 2, 8, and the orientation of the first display screen 4 can be measured using a sensor 42 in the first electronic device 2. As noted above, the measurement of the orientation can be a measurement of the orientation of the first display screen 4 in three dimensions, and the measurement of the position of the first electronic device 2 relative to the second electronic device 8 can be measurements of the absolute position of the two electronic devices 2, 8, or a measurement of the distance between the devices and an indication of the direction from one device to the other.

In some embodiments, a measurement of the orientation of the second display screen 10 can also be obtained in step 101. The orientation of the second display screen 10 can be measured using a sensor 42 in the second electronic device 8.

In step 103 the obtained measurements are used to determine whether a second user 12 using the second electronic device 8 can view the first display screen 4. Some exemplary ways of implementing step 103 are described in more detail below. In some embodiments, the second user 12 using the second electronic device 8 includes the second user 12 viewing the second display screen 10.

Next, in step 105, the display of information on the first display screen 4 is controlled based on whether the second user 12 can view the first display screen 4.

Step 105 can comprise changing the information displayed on the first display screen 4 if it is determined that the second user 12 can view the first display screen 4. That is, the information displayed on the first display screen 4 is changed from the information that is or was displayed previously when the second user 12 could not see the first display screen 4. Likewise, if it was previously determined that the second user 12 could view the first display screen 4 and it is determined in step 105 that the second user 12 now cannot view the first display screen 4, the information displayed on the first display screen 4 can be changed.

The nature of the change in information in step 105 can depend on various factors, for example the type of information being displayed, the sensitivity/confidentiality of the information, the context in which the electronic devices 2, 8 are being used (e.g. in a test/assessment, as part of a game, etc.), etc. The change in information may be a change of all of the information displayed on the first display screen 4 or just some of the information.

In some embodiments the change in information in step 105 can comprise stopping or preventing the display of information (or certain parts or types of the information) on the first display screen 4 if the second user 12 can view the first display screen 4. In some embodiments, stopping or preventing the display of information on the first display screen 4 can comprise controlling the first electronic device 2 to switch off the first display screen 4. In this case, the display of information on the first display screen 4 may only be allowed or permitted if the second user 12 cannot view the first display screen 4.

In some embodiments, step 105 can comprise presenting a message and/or image on the first display screen 4 if it is determined that that the second user 12 can view the first display screen 4, with the message and/or image indicating that the second user 12 may be viewing the first display screen 4 and that action should be taken to ensure that the second user 12 cannot see the first display screen 4.

The method in FIG. 4 is preferably performed continuously or frequently during the use of the first electronic device 2 so that the display of information can be controlled as the orientation and/or relative position of the electronic devices 2, 8 changes.

In some embodiments the method is performed in the first electronic device 2, in which case the step of obtaining measurements (step 101) can comprise receiving measurements of the position and/or orientation of the second display screen 10 of the second electronic device 8 from sensors in the second electronic device 8 (for example via short-range wireless communications or via a cellular communications network) or from another device, such as a server 16.

In alternative embodiments, the method is performed in the second electronic device 8 in which case the step of obtaining measurements (step 101) can comprise receiving measurements of the position and/or orientation of the first display screen 4 of the first electronic device 2 from sensors in the first electronic device 2 (for example via short-range wireless communications or via a cellular communications network) or from another device, such as a server 16. The step of controlling the display of information on the first display screen 4 (step 105) can comprise sending a suitable control signal from the second electronic device 8 to the first electronic device 2 (for example via the means suggested above for step 101). On receipt of this control signal, the first electronic device 2 can control the first display screen 4 to display the appropriate information.

In other alternative embodiments, the method can be performed in an electronic device other than the first electronic device 2 and the second electronic device 8, for example in server 16, in which case the step of obtaining measurements (step 101) can comprise receiving measurements of the position and/or orientation of the first display screen 4 from sensors in the first electronic device 2 and receiving measurements of the position and/or orientation of the second display screen 10 from sensors in the second electronic device 8. The step of controlling the display of information on the first display screen 4 (step 105) can comprise sending a suitable control signal to the first electronic device 2. On receipt of this control signal, the first electronic device 2 can control the first display screen 4 to display the appropriate information.

Figure 5:
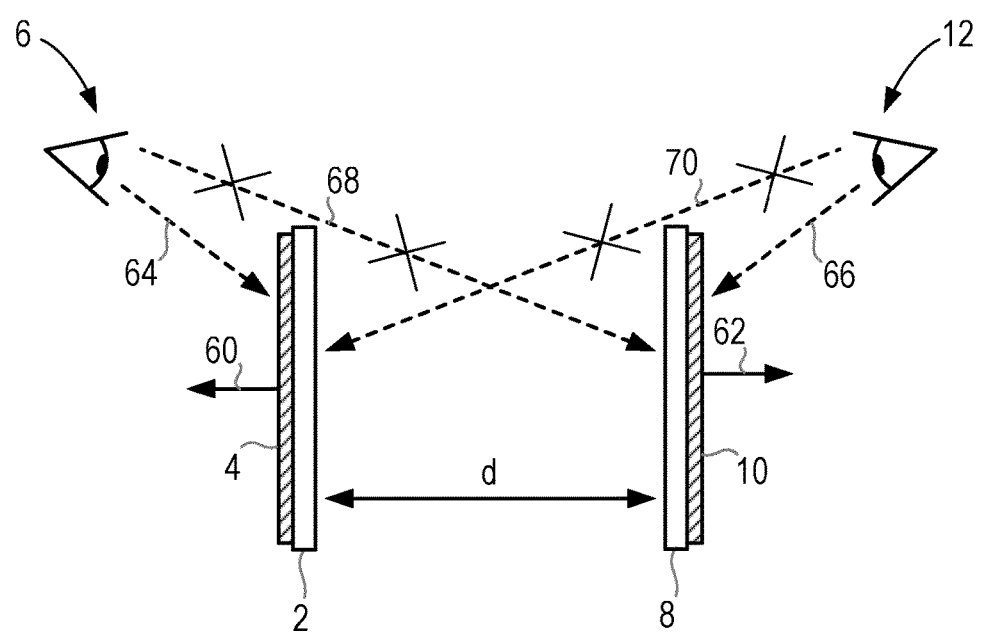
FIG. 5 illustrates an arrangement of two electronic devices in which users of either electronic device cannot view a display screen of the other electronic device.

FIG. 5 illustrates a side view of two electronic devices 2, 8 that are being used by respective users 6, 12 in an arrangement that means neither user 6, 12 can see the display screen 4, 10 of the other electronic device 2, 8. In this case, the first display screen 4 is generally oriented so that the back of the first electronic device 2 (i.e. the side of the first electronic device 2 that is opposite the side of the first electronic device 2 having the first display screen 4) is facing the second electronic device 8 that is spaced some distance d from the first electronic device 2, so someone using the second electronic device 8 (e.g. holding the second electronic device 8 and/or looking at the second display screen 10) will not be able to directly view the first display screen 4.

Although the second electronic device 8 is shown in FIG. 5 as being oriented so that the second display screen 10 is facing away from the first electronic device 2 (as indicated in FIG. 5 by arrow 62), it will be appreciated that for the purposes of the method of FIG. 4 this does not have to be the case and a user of the second electronic device 8 that is spaced a sufficient distance d from the first electronic device 2 will not be able to view the first display screen 4 regardless of the orientation of the second electronic device 8 (since the first display screen 4 is facing away from the second electronic device 8).

In FIG. 5, arrows 64 and 66 indicate that the first user 6 and second user 12 are viewing (i.e. have line-of-sight of) the first display screen 4 and second display screen 10 respectively. Crossed arrows 68 and 70 indicate that the first user 6 and second user 12 cannot view the second display screen 10 and first display screen 4 respectively.

Figure 6A:
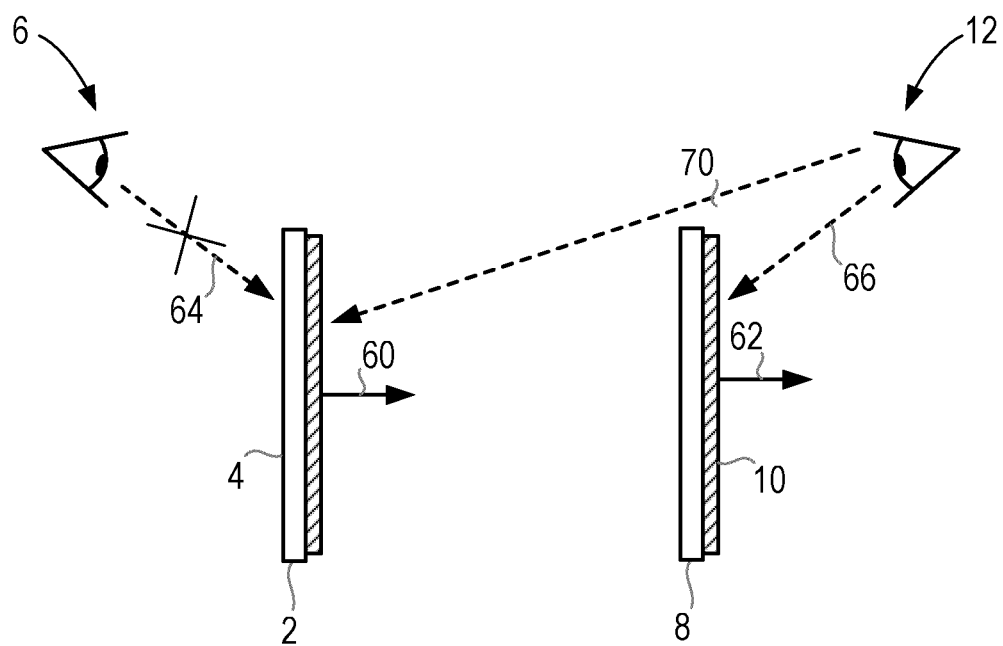
FIGS. 6(a)-(c) illustrate alternative arrangements of two electronic devices in which a display screen of a first electronic device can be viewed by a user of a second electronic device.
Figure 6B:
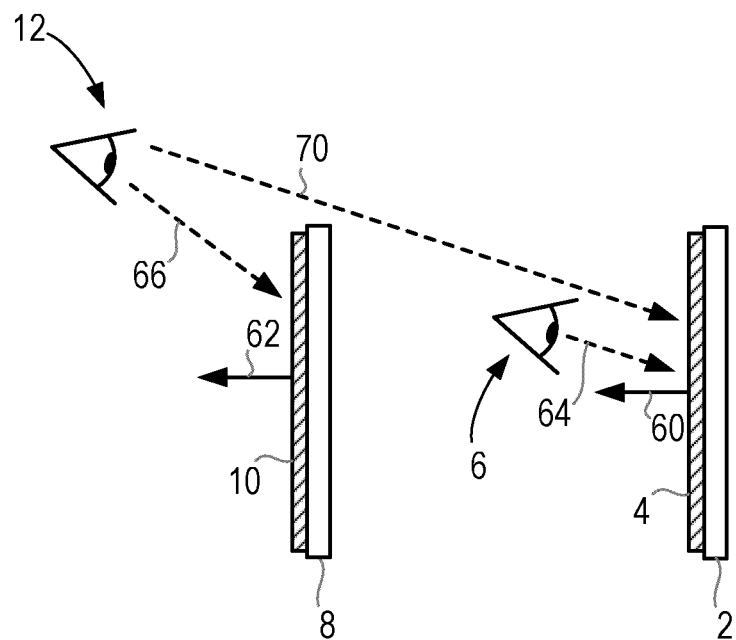

FIGS. 6(*a*), (*b*) and (*c*) illustrate three situations in which the second user 12 of the second electronic device 8 can view the first display screen 4 (i.e. has line-of-sight to the first display screen 4) as well being able to view the second display screen 10, and in which the display of information on the first display screen 4 may be changed from when the electronic devices 2, 8 are in the arrangement shown in FIG. 5.

In FIG. 6(*a*), the first electronic device 2 is oriented so that the first display screen 4 is generally facing the second electronic device 8 (i.e. the first display screen 4 is generally facing in the opposite direction to that shown in FIG. 5), and thus the second user 12 can see both display screens from their location (as indicated by arrows 66, 70).

In FIG. 6(*b*), the second user 12 (and the second electronic device 8) is positioned behind the first user 6 and the first electronic device 2 with the electronic devices 2, 8 arranged in generally the same orientation (i.e. they are both generally facing the same direction) so that the second user 12 can view both display screens 4, 10 (for example the second user 12 may be able to look over the shoulder of the first user 6 at the first display screen 4). This is indicated by arrows 66, 70.

The situation in FIG. 6(*c*) is similar to FIG. 6(*b*), although in this situation the second electronic device 8 is oriented in the opposite direction to the first electronic device 2 (as in FIG. 5) so that when the second user 12 is facing the second display screen 10 they would be facing the opposite direction to the first electronic device 2. However, in this situation it is possible for the second user 12 to view the first display screen 4 simply by turning their head, so the arrangement of the electronic devices 2, 8 means that the second user 12 can view the first display screen 4 and thus the display of information on the first display screen 4 may be changed.

Figure 7:
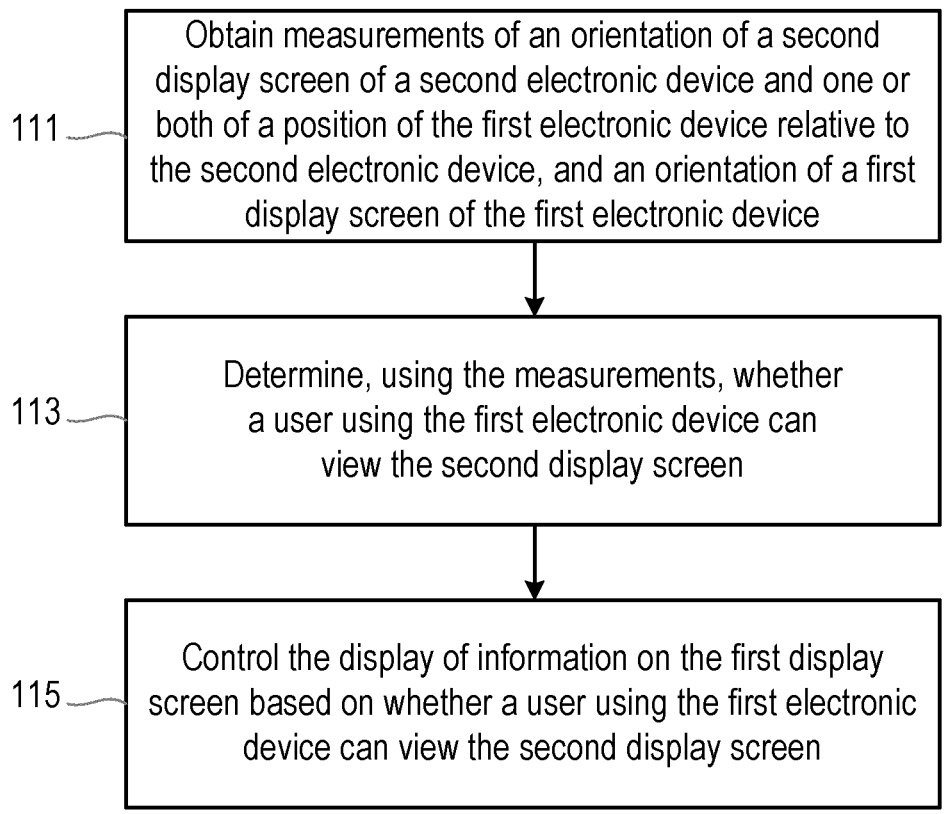
FIG. 7 is a flow chart illustrating a method according to a second embodiment.

The flow chart in FIG. 7 illustrates a method of operating a first electronic device 2 according to another embodiment of the invention. In this embodiment, the display of information on the first display screen 4 is controlled based on whether the first user 6 of the first electronic device 2 can view the second display screen 10. It will be appreciated that it is not necessary to determine whether the user of the first electronic device 2 is also viewing the display screen 4 of the first electronic device 2, although in some embodiments this is determined.

In a first step, step 111, measurements of a position of the first electronic device 2 relative to the second electronic device 8 and an orientation of the second display screen 10 are obtained. The position can be measured using a sensor or sensors 40, 44 in one or both of the first and second electronic devices 2, 8, and the orientation of the second display screen 10 can be measured using a sensor 42 in the second electronic device 8. As noted above, the measurement of the orientation can be a measurement of the orientation of the second display screen 10 in three dimensions, and the measurement of the position of the first electronic device 2 relative to the second electronic device 8 can be measurements of the absolute position of the two electronic devices 2, 8, or a measurement of the distance between the devices and an indication of the direction from one device to the other.

In some embodiments, a measurement of the orientation of the first display screen 4 can also be obtained in step 111. The orientation of the first display screen 4 can be measured using a sensor 42 in the first electronic device 2.

In step 113 the obtained measurements are used to determine whether the first user 6 using the first electronic device 2 can view the second display screen 10. Some exemplary ways of implementing step 113 are described in more detail below. In some embodiments, the first user 6 using the first electronic device 2 includes the first user 6 viewing the first display screen 4.

Next, in step 115, the display of information on the first display screen 4 is controlled based on whether the first user 6 viewing the first display screen 4 can view the second display screen 10. Step 115 can be implemented in a similar way to step 105 described above for when the second user 12 can view the first display screen 4.

In some embodiments, step 115 can comprise presenting a message and/or image on the first display screen 4 if it is determined that that the first user 6 can view the second display screen 10, with the message and/or image indicating that the first user 6 may be viewing the second display screen 10 and that action should be taken to ensure that they cannot see the second display screen 10.

As with the method in FIG. 4, the method in FIG. 7 is preferably performed continuously or frequently during the use of the first electronic device 2 so that the display of information can be controlled as the orientation and/or relative position of the electronic devices 2, 8 changes.

Also as with the method in FIG. 4, the method in FIG. 7 can be performed in the first electronic device 2, the second electronic device 8 or an electronic device other than the first electronic device 2 and the second electronic device 8 (for example in server 16).

As noted above, FIG. 5 illustrates two electronic devices 2, 8 that are being used by respective users 6, 12 in an arrangement that means neither user 6, 12 can see the display screen 4, 10 of the other electronic device 2, 8. In this case, the second display screen 10 is generally oriented so that the back of the second electronic device 8 is facing the first electronic device 2 that is spaced some distance d from the second electronic device 8, so someone using the first electronic device 2 (e.g. holding the first electronic device 2, looking at the first display screen 4) will not be able to directly view the second display screen 10.

With respect to the method in FIG. 7, although the first electronic device 2 is shown in FIG. 5 as being oriented so that the first display screen 4 is facing away from the second electronic device 8 (as indicated in FIG. 5 by arrow 60), it will be appreciated that for the purposes of the method of FIG. 7 this does not have to be the case and a user of the first electronic device 2 that is spaced a sufficient distance d from the second electronic device 8 will not be able to view the second display screen 10 regardless of the orientation of the first electronic device 2 (since the second display screen 10 is facing away from the first electronic device 2).

FIGS. 8(*a*) and (*b*) illustrate two situations in which the first user 6 of the first electronic device 2 can view the second display screen 10 as well being able to view the first display screen 4, and in which the display of information on the first display screen 4 may be changed from when the electronic devices 2, 8 are in the arrangement shown in FIG. 5.

Figure 8A:
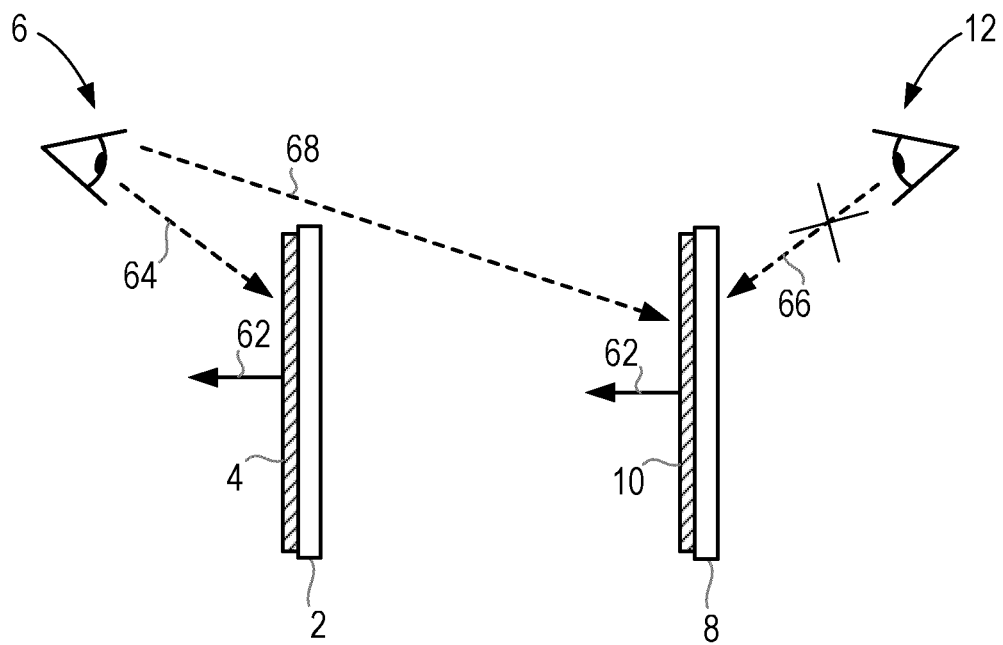
FIGS. 8(a) and (b) illustrate alternative arrangements of two electronic devices in which a user of a first electronic device can view a display screen of a second electronic device.

In FIG. 8(a), the second electronic device 8 is oriented so that the second display screen 10 is generally facing the first electronic device 2 (i.e. the second display screen 10 is generally facing in the opposite direction to that shown in FIG. 5), and thus the first user 6 can see both display screens from their location (as indicated by arrows 64, 68).

Figure 8B:
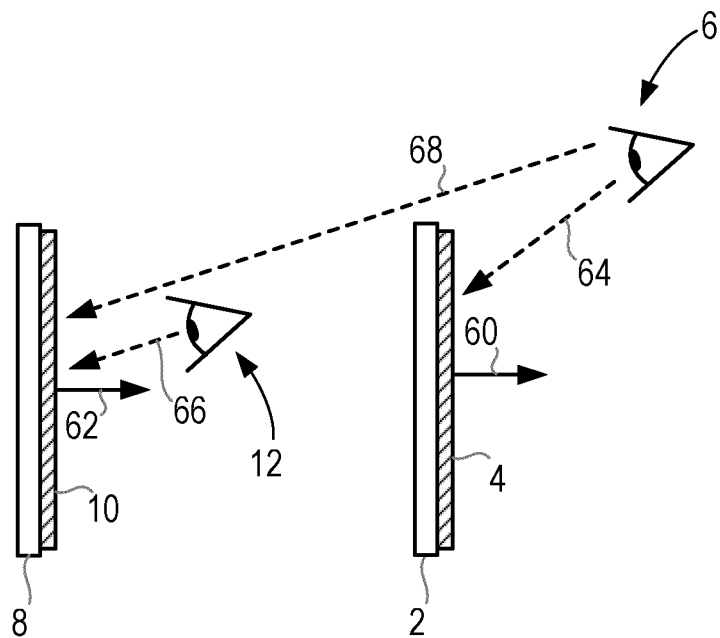

In FIG. 8(b), the first user 6 (and the first electronic device 2) is positioned behind the second user 12 and the second electronic device 8 with the electronic devices 2, 8 arranged in generally the same orientation (i.e. they are both generally facing the same direction) so that the first user 6 can view both display screens 4, 10 (for example the first user 6 may be able to look over the shoulder of the second user 12 at the second display screen 10). This is indicated by arrows 64, 68.

Figure 6C:
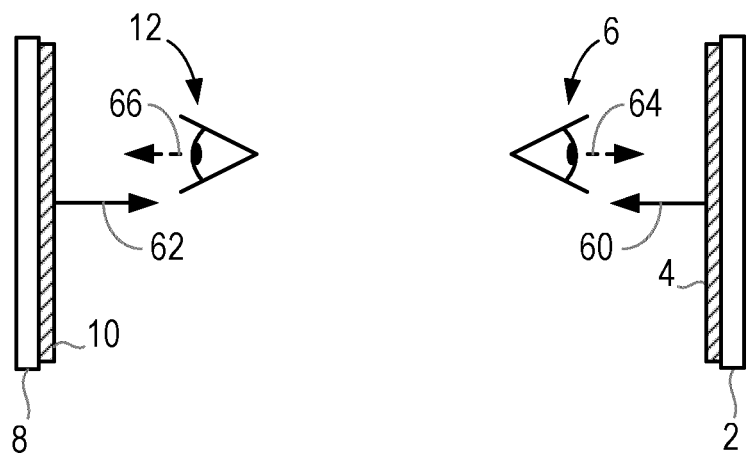

The situation shown in FIG. 6(c) is also possible, where the first electronic device 2 is oriented in the opposite direction to the second electronic device 8 (as in FIG. 5) so that when the first user 6 is facing the first display screen 4 they would be facing the opposite direction to the second electronic device 8. However, in this situation it is possible for the first user 6 to view the second display screen 10 simply by turning their head, so the arrangement of the electronic devices 2, 8 means that the first user 6 can view the second display screen 10 and thus the display of information on the first display screen 4 may be changed.

In some embodiments, the methods of FIGS. 4 and 7 can be performed together, which means that the display of information on the first display screen 4 can be controlled based on whether the first user 6 can view the second display screen 10, and whether the second user 12 can view the first display screen 4. In some implementations, the display of information on the first display screen 4 may be changed if either of the first user 6 can view the second display screen 10 or the second user 12 can view the first display screen 4. In other implementations, the display of information on the first display screen 4 may be only be changed if both the first user 6 can view the second display screen 10 and the second user 12 can view the first display screen 4.

In some embodiments, the methods of FIGS. 4 and/or 7 can be performed for both electronic devices 2, 8 (i.e. the display of information on both the first display screen 4 and the second display screen 10 can be controlled based on either or both of whether the first user 6 can view the second display screen 10 and a second user 12 can view the first display screen 4). In this case, suitable control signals can be sent to the electronic devices 2, 8 or between the electronic devices 2, 8.

As noted above, in step 103, it is determined whether the second user 12 can view the first display screen 4, and in step 113 it is determined whether the first user 6 can view the second display screen 10. Some exemplary ways in which these steps can be implemented are set out below.

In some embodiments, these steps can be implemented by determining an initial set of measurements of the position and/or orientation of the electronic devices 2, 8 in which either or both of the first user 6 cannot view the second display screen 10 and the second user 12 cannot view the first display screen 4, and then analyzing the measurements obtained in step 101/111 to determine if the orientation and/or position of one or both of the devices 2, 8 has changed or changes significantly or by more than an appropriate threshold amount (e.g. an orientation change of more than 60°) such that the first user 6 could view the second display screen 10 or the second user 12 could view the first display screen 4.

The initial set of measurements can be obtained when the electronic devices 2, 8 are first paired or linked to enable the method according to the invention to be used (for example when a test, assessment or game is to be started), or they can be obtained during a calibration procedure in which one or both users 6, 12 verify that the electronic devices 2, 8 are in an appropriate arrangement (e.g. as shown in FIG. 5).

The pairing or linking of the electronic devices 2, 8 may be performed by arranging the electronic devices 2, 8 in a particular known configuration (e.g. by touching or tapping the devices 2, 8 together), and the initial measurements can be made while the devices 2, 8 are in this configuration. In a preferred embodiment, the pairing or linking of the devices 2, 8 can be performed by touching the back of one of the devices to the back of the other device and using a short range communication technique (e.g. NFC) to pair the devices 2, 8. Since this pairing can only be performed by placing the devices 2, 8 back-to-back, the orientation measurements will represent an initial arrangement of the devices 2, 8 in which neither user 6, 12 can see both display screens.

One alternative way of implementing these steps uses the measurement of the orientation of an electronic device and the position of that electronic device relative to the other electronic device to provide an indication of the position of the relevant user (the one that is the subject of step 103 or 113) and an indication of whether the display screen of the other electronic device is visible from the position of that user.

For example, to determine whether the second user 12 using the second electronic device 8 can also view the first display screen 4 (in step 103), the measurement of the position of the first electronic device 2 relative to the second electronic device 8 can be used to provide an indication of the location of the second user 12 (i.e. the same location as the second electronic device 8 since it is assumed that the second user 12 is holding or otherwise using the second electronic device 8), and the orientation of the first electronic device 2/first display screen 4 can be used to determine whether the first display screen 4 is facing or visible at the location of the second user 12.

It will be appreciated that this implementation effectively models the physical arrangement of the electronic devices 2, 8 and estimates whether the second user 12 is within a viewing region of the first display screen 4. The viewing region can be defined by the orientation of the first display screen 4 and the viewing angle of the first display screen 4 and gives a range of positions in front of the first display screen 4 in which the first display screen 4 can be viewed. If the position of the second user 12 places them in this viewing region, then they can be determined to be able to view the first display screen 4. In some embodiments, the viewing region can be assumed to be anywhere in front of the first display screen 4 (i.e. anywhere within 90° of an axis extending perpendicularly to the plane of the display screen).

In another example, to determine whether the first user 6 using the first electronic device 2 can view the second display screen 10 (in step 113), the measurement of the position of the first electronic device 2 relative to the second electronic device 8 can be used to provide an indication of the location of the first user 6 (i.e. the same location as the first electronic device 2 since it is assumed that the first user 6 is holding or otherwise using the first electronic device 2), and the orientation of the second electronic device 8/second display screen 10 can be used to determine whether the second display screen 10 is facing or visible at the location of the first user 6.

In the above methods it is assumed that the users of the electronic devices 2, 8 are actually using the electronic devices 2, 8 (which allows the assumption to be made that the position of the users is the same as that of their respective electronic devices 2, 8). However, it is possible with these methods that one or both of the users puts their electronic device 2, 8 down (e.g. on a table) in an orientation that results in information continuing to be displayed on the first display screen 4, and then the user moves to a position where they can see the display screen of the other electronic device 2, 8.

Therefore, to prevent this type of cheating or collaboration between the users some embodiments provide an additional step of determining whether the first electronic device 2 and/or the second electronic device 8 are being held or otherwise used by a user, and then controlling the display of information on the first display screen 4 accordingly. For example in the method of FIG. 4 if it is determined that the second electronic device 8 is not being held or otherwise used by a user, the display of information on the first display screen 4 can be controlled in the same way as if it had been determined that the second user 12 can view the first display screen 4 (e.g. the displayed information can be changed, the display screen can be switched off, etc.). Similarly for the method of FIG. 7 if it is determined that the first electronic device 2 is not being held or otherwise used by a user, the display of information on the first display screen 4 can be controlled in the same way as if it had been determined that the first user 6 can view the second display screen 10.

Those skilled in the art will be aware of numerous techniques that can be used to determine if an electronic device 2, 8 is being held or otherwise used by a user. For example, a signal from a motion sensor (e.g. an accelerometer) in the electronic device can be analyzed to determine if electronic device 2, 8 is moving (which indicates that it is being held by a user) and/or if the electronic device 2, 8 is oriented so that the device is laid flat (e.g. if it has been placed on a table), which may indicate that it is not being held by a user. In addition or alternatively, the electronic device 2, 8 may include a sensor that detects contact between the electronic device 2, 8 with the skin of the user (e.g. a skin conductivity sensor). As another alternative, the electronic device 2, 8 can monitor an amount of time since a user last interacted with the electronic device 2, 8 (e.g. by pushing a button, touching the screen, etc.) and consider that the electronic device 2, 8 is not being held or used by the user if more than a threshold amount of time has passed since the last user interaction. As a further alternative, images from a camera or light sensor on the electronic device 2, 8 could be processed to determine if a user is holding or otherwise close to the electronic device 2, 8. For example, if the electronic device 2, 8 has a camera in the front face of the device (so that it faces a user), the images can be processed to determine if a user is in front of the device. In some embodiments, the images from the camera can be processed to determine if a user is actually looking at the display screen. Those skilled in the art will be aware of various object/shape recognition, facial recognition or eye-tracking techniques that can be used for processing camera images in these embodiments.

Where a signal from an accelerometer is analyzed to determine if the electronic device 2, 8 is moving, the signal can be processed to determine an absolute energy. Absolute energy can be determined by filtering an accelerometer signal (e.g. covering a short time period such as a few seconds) for comparison with a threshold. The threshold can be set at a value that takes into account the noise in the accelerometer signal. This noise may be specific to a particular type of accelerometer or electronic device and this a device-specific calibration may be required.

In a further embodiment, images from a camera or light sensor on the electronic device 2, 8 could be processed to determine if more than one user can see display screen of the electronic device. For example, if the electronic device 2, 8 has a camera in the front face of the device (so that it faces a user), the images can be processed to determine if two people are in front of the device. Those skilled in the art will be aware of various object/shape recognition or facial recognition that can be used for processing camera images in this embodiment.

As described above, the invention can be used in electronic devices 2, 8 that are used to carry out a health-based assessment on a subject to reduce the chances of the subject cheating or otherwise gaining some advantage in the test by the subject viewing the display screen of an assessor's electronic device or the assessor or test supervisor viewing the display screen of the subject's electronic device. An exemplary assessment process that makes use of various embodiments of the invention presented herein is described below. In this exemplary assessment technique, the subject corresponds to the first user 6, the test supervisor or assessor corresponds to the second user 12, the subject's electronic device 2 is a tablet and the supervisor's electronic device 8 is a tablet.

The subject's tablet 2 displays the test questions or tasks that have to be completed by the subject 6 during the assessment. The supervisor's tablet 8 is used by the supervisor to start the test and follow the progress of the subject through the assessment. Both devices 2, 8 are preferably general-purpose tablets running a suitable application program. The application programs communicate with a server 16 via the Internet that provides the test data and collects the results.

While the test is being carried out, the subject 6 is required to look at the display screen 4 of the tablet 2 and the supervisor 12 is required to look at the display screen 10 of their device 8. According to the invention described herein, the location and orientations of the two devices 2, 8 are measured and the measurements analyzed to ensure that no person 6, 12 can view both display screens at the same time. The supervisor 12 must keep looking at their device 8 and may be required to provide inputs to their device 8 to confirm various steps of the assessment process.

The exemplary assessment process is as follows:

The assessment test is initiated, either by the subject 6 using their tablet 2 or by the supervisor 12 using their tablet 8. A log-in to the remote server 16 may be required by one or both users 6, 12. The tablet 8 may request (via suitable information displayed on its display screen 10) that the supervisor 12 "taps in" to start the test. This requires the supervisor 12 to perform an NFC tap with the subject's tablet 2, with the two devices back-to-back (i.e. so that an NFC connected is established between the devices 2, 8). This NFC tap results in the tablets 2, 8 being paired or associated with each other. Detection of this tap can be used to confirm an initial 'acceptable' alignment of the two devices 2, 8 (i.e. the display screens 4, 10 are facing in opposite directions since the devices 2, 8 are back-to-back) and the orientations of the devices 2, 8 at the time of this tap (as determined by respective orientation sensors 42) can be measured and stored.

The supervisor 12 can take their device 8 and move away from the subject 6 while generally maintaining the acceptable alignment of the two devices 2, 8 so that the subject 6 cannot see the display screen 10 of the supervisor's tablet 8 and the supervisor 12 cannot see the display screen 4 of the subject's tablet 2. The test starts on the subject's tablet 2 (possibly in response to the supervisor 12 initiating the test using their tablet 8), with test data provided the subject's tablet 2 from the network server 16.

Questions or tasks can be provided to the subject 6 one at a time and the subject 6 uses their tablet 2 to provide their response. The supervisor may be required to confirm the delivery of each question in turn via their tablet 8, or to select questions that the subject 6 can pass unanswered. The supervisor 12 need not see the answers provided by the subject 6 during the test. This can be made clear to both users 6, 12 by information provided to each user via their display screens 4, 10.

While the test is being performed, measurements of the orientation of both devices 2, 8 are collected and analyzed, and if it is detected that either of the two devices 2, 8 is rotated such that both display screens 4, 10 are facing the same way (so that they could both be viewed by a single user), the subject's tablet 2 is controlled so that test content is no longer displayed on their display screen 4. Optionally a message can be displayed to the subject 6 along the lines of "Please ensure that the supervisor cannot see your display screen". A similar message can be displayed to the supervisor via their display screen 10. Measurements of the position or relative position of the devices 2, 8 or displacement of the devices 2, 8 from the initial positions can also be monitored to determine if one of the users 6, 12 can see the display screen of the other device 2, 8.

Optionally, each device 2, 8 can determine if it is no longer being held by the user 6, 12 (for example by analyzing a signal from a motion sensor in the device), as an indication that a device is no longer being held could mean that the person using it has moved to a position where they can see the other display screen.

Optionally, cameras on the rear face of one or both devices 2, 8 can be used to ensure an appropriate alignment of the devices. For example object recognition techniques could be used on the camera output to determine if the back of the other device 2, 8 is visible, and if not it could be determined that the devices 2, 8 are not in an appropriate alignment and the display of information on one or both devices controlled accordingly.

Optionally, cameras on the front face of one or both devices 2, 8 can be used to determine if each user 6, 12 continues to look at their display screen during the test.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

Various exemplary embodiments are set out in the following statements:

1. A method of controlling the operation of a first electronic device having a first display screen, the method comprising:

obtaining measurements of a position of the first electronic device relative to a second electronic device, an orientation of the first display screen, and/or an orientation of a second display screen of a second electronic device;

determining, using the obtained measurements, one or both of (i) whether a first user using the first electronic device can view the second display screen, and (ii) whether a second user using the second electronic device can view the first display screen; and controlling the display of information on the first display screen based on the result of the step of determining.

2. A method as in statement 1, wherein the step of controlling the display of information on the first display screen comprises:

changing the information displayed on the first display screen if it is determined that the first user can view the second display screen, and/or if it is determined that the second user can view the first display screen.

3. A method as in statement 1, wherein the step of controlling the display of information on the first display screen comprises:

causing the presentation of first information using the first display screen if it is determined that the first user cannot view the second display screen, and/or if it is determined that the second user cannot view the first display screen; and causing the presentation of second information using the first display screen if it is determined that the first user can view the second display screen, and/or it is determined that the second user can view the first display screen.

4. A method as in statement 1, wherein the step of controlling the display of information on the first display screen comprises:

allowing the display of information on the first display screen if it is determined that the first user cannot view the second display screen, and/or if it is determined that the second user cannot view the first display screen; and stopping or preventing the display of information on the first display screen if it is determined that the first user can view the second display screen, and/or it is determined that the second user can view the first display screen.

5. A method as in any of statements 1-4, wherein the step of determining comprises:

using the orientation of the first display screen and/or position of the first electronic device relative to the second electronic device to estimate a position of the first user when using the first electronic device; and using the orientation of the second display screen, the position of the first electronic device relative to a second electronic device and the estimated position of the first user to determine if the first user can view the second display screen.

6. A method as in any of statements 1-5, wherein the step of determining comprises:

using the orientation of the second display screen and/or position of the first electronic device relative to the second electronic device to estimate a position of the second user when using the second electronic device; and using the orientation of the first display screen, the position of the first electronic device relative to a second electronic device, and the estimated position of the second user to determine if the second user can view the first display screen.

7. A method as in any of statements 1-6, wherein an initial set of measurements are obtained when the first electronic device and the second electronic device are in an arrangement in which the first user cannot view the second display screen, and/or in which the second user cannot view the first display screen; and wherein the step of determining comprises determining that the first user can view the second display screen and/or that the second user can view the first display screen if the orientation of the first display screen and/or the orientation of the second display screen change from the initial set of measurements by more than a threshold amount.

8. A method as in any of statements 1-9, the method further comprising:

determining if the first electronic device is being held or used by a user; wherein the step of controlling further comprises controlling the display of information on the first display screen based on whether the first electronic device is being held or used by a user.

9. A method as in any of statements 1-8, the method further comprising:

determining if the second electronic device is being held or used by a user;

wherein the step of controlling further comprises controlling the display of information on the first display screen based on whether the second electronic device is being held or used by a user.

10. A method of controlling the operation of a first electronic device having a first display screen and a second electronic device having a second display screen, the method comprising:

controlling the operation of the first electronic device according to the method of any of statements 1-9; and controlling the display of information on the second display screen based on (i) whether the first user can view the second display screen, and/or (ii) whether the second user can view the first display screen.

11. A computer program product comprising a computer readable medium having computer readable code embodied therein, the computer readable code being configured such that, on execution by a suitable computer or processor, the computer or processor is caused to perform the method of any of statements 1-10.

12. An apparatus, for use in controlling the operation of a first electronic device having a first display screen, the apparatus comprising a processing unit that is configured to:

obtain measurements of a position of the first electronic device relative to a second electronic device, an orientation of the first display screen, and/or an orientation of a second display screen of a second electronic device;

determine, using the obtained measurements, one or both of (i) whether a first user using the first electronic device can view the second display screen, and (ii) whether a second user using the second electronic device can view the first display screen; and control the display of information on the first display screen based on (i) whether the first user can view the second display screen, and (ii) whether the second user can view the first display screen.

13. An apparatus as in statement 12, wherein the processing unit is configured to determine whether the first user can view the second display screen by:

estimating a position of the first user when using the first electronic device using the orientation of the first display screen and/or position of the first electronic device relative to the second electronic device; and using the orientation of the second display screen, the position of the first electronic device relative to the second electronic device and the estimated position of the first user to determine if the first user can view the second display screen.

14. An apparatus as in statement 12 or 13, wherein the processing unit is configured to determine whether the second user can view the first display screen by:

estimating a position of the second user when using the second electronic device using the orientation of the second display screen and/or position of the first electronic device relative to the second electronic device; and using the orientation of the first display screen, the position of the first electronic device relative to a second electronic device and the estimated position of the second user to determine if the second user can view the first display screen.

15. An apparatus as in any of statements 12-14, wherein the processing unit is configured to obtain an initial set of measurements when the first electronic device and the second electronic device are in an arrangement in which the first user cannot view the second display screen, and/or in which the second user cannot view the first display screen; and the processing unit is configured to determine that the first user can view the second display screen and/or that the second user can view the first display screen if the orientation of the first display screen and/or the orientation of the second display screen change from the initial set of measurements by more than a threshold amount.

The invention claimed is:

1. A method of controlling the operation of a first electronic device having a first display screen, the method comprising:

determining if the first display screen is in use by a first user;

obtaining measurements of an orientation of a second display screen of a second electronic device, and one or both of a position of the first electronic device relative to the second electronic device and an orientation of the first display screen;

determining, using the obtained measurements, whether the first user using the first electronic device can view the second display screen; and controlling the display of information on the first display screen based on the result of the step of determining;

wherein the step of determining comprises:

using the orientation of the first display screen and/or position of the first electronic device relative to the second electronic device to estimate a position of the first user when using the first electronic device; and determining if the second display screen can be viewed from the estimated position of the first user using the orientation of the second display screen.

2. The method as claimed in claim 1, wherein the step of controlling the display of information on the first display screen comprises:

changing the information displayed on the first display screen if it is determined that the first user can view the second display screen.

3. The method as claimed in claim 1, wherein the step of controlling the display of information on the first display screen comprises:

causing the presentation of first information using the first display screen if it is determined that the first user cannot view the second display screen; and causing the presentation of second information using the first display screen if it is determined that the first user can view the second display screen.

4. The method as claimed in claim 1, wherein the step of controlling the display of information on the first display screen comprises:
allowing the display of information on the first display screen if it is determined that the first user cannot view the second display screen; and
stopping or preventing the display of information on the first display screen if it is determined that the first user can view the second display screen.

5. The method as claimed in claim 1, wherein an initial set of measurements are obtained when the first electronic device and the second electronic device are in an arrangement in which the first user cannot view the second display screen; and
wherein the step of determining comprises determining that the first user can view the second display screen if the orientation of the first display screen and/or the orientation of the second display screen change from the initial set of measurements by more than a threshold amount.

6. The method as claimed in claim 1, the method further comprising:
determining if the first electronic device is being held or used by a user;
wherein the step of controlling further comprises controlling the display of information on the first display screen based on whether the first electronic device is being held or used by a user.

7. The method as claimed in claim 1, the method further comprising:
determining if the second electronic device is being held or used by a user;
wherein the step of controlling further comprises controlling the display of information on the first display screen based on whether the second electronic device is being held or used by a user.

8. A method of controlling the operation of a first electronic device having a first display screen and a second electronic device having a second display screen, the method comprising:
controlling the operation of the first electronic device according to the method of claim 1; and
controlling the display of information on the second display screen based on whether the first user can view the second display screen.

9. A computer program product comprising a computer readable medium having computer readable code embodied therein, the computer readable code being configured such that, on execution by a suitable computer or processor, the computer or processor is caused to perform the method of claim 1.

10. A method of controlling the operation of a first electronic device having a first display screen, the method comprising:
determining if the first display screen is in use by a first user;
obtaining measurements of an orientation of the first display screen, and one or both of a position of the first electronic device relative to a second electronic device and an orientation of a second display screen of the second electronic device;
determining, using the obtained measurements, whether a second user using the second electronic device can view the first display screen; and controlling the display of information on the first display screen based on the result of the step of determining;
wherein the step of determining comprises:
using the orientation of the second display screen and/or position of the first electronic device relative to the second electronic device to estimate a position of the second user when using the second electronic device; and
determining if the first display screen can be viewed from the estimated position of the second user using the orientation of the first display screen.

11. The method as claimed in claim 10, wherein the step of controlling the display of information on the first display screen comprises:
changing the information displayed on the first display screen if it is determined that the second user can view the first display screen.

12. The method as claimed in claim 10, wherein the step of controlling the display of information on the first display screen comprises:
allowing the display of information on the first display screen if it is determined that the second user cannot view the first display screen; and
stopping or preventing the display of information on the first display screen if it is determined that the second user can view the first display screen.

13. The method as claimed in claim 10, wherein an initial set of measurements are obtained when the first electronic device and the second electronic device are in an arrangement in which the second user cannot view the first display screen; and
wherein the step of determining comprises determining that the second user can view the first display screen if the orientation of the first display screen and/or the orientation of the second display screen change from the initial set of measurements by more than a threshold amount.

14. The method as claimed in claim 10, the method further comprising:
determining if the first electronic device is being held or used by a user;
wherein the step of controlling further comprises controlling the display of information on the first display screen based on whether the first electronic device is being held or used by a user.

15. The method as claimed in claim 10, the method further comprising:
determining if the second electronic device is being held or used by a user;
wherein the step of controlling further comprises controlling the display of information on the first display screen based on whether the second electronic device is being held or used by a user.

16. The method of controlling the operation of a first electronic device having a first display screen and a second electronic device having a second display screen, the method comprising:
controlling the operation of the first electronic device according to the method of claim 10; and
controlling the display of information on the second display screen based on whether the second user can view the first display screen.

17. An apparatus, for controlling the operation of a first electronic device having a first display screen, the apparatus comprising a processing unit that is configured to:
obtain measurements of an orientation of a second display screen of a second electronic device, and one or both of a position of the first electronic device relative to the second electronic device and an orientation of the first display screen;

determine, using the obtained measurements, whether a first user using the first electronic device can view the second display screen; and control the display of information on the first display screen based on whether the first user can view the second display screen;

wherein the processing unit is configured to:

use the orientation of the first display screen and/or position of the first electronic device relative to the second electronic device to estimate a position of the first user when using the first electronic device; and determine if the second display screen can be viewed from the estimated position of the first user using the orientation of the second display screen.

18. The apparatus as claimed in claim 17, wherein the processing unit is configured to determine whether the first user can view the second display screen by:

estimating a position of the first user when using the first electronic device using the orientation of the first display screen and/or position of the first electronic device relative to the second electronic device; and using the orientation of the second display screen, the position of the first electronic device relative to the second electronic device and the estimated position of the first user to determine if the first user can view the second display screen.

19. The apparatus as claimed in claim 17, wherein the processing unit is configured to obtain an initial set of measurements when the first electronic device and the second electronic device are in an arrangement in which the first user cannot view the second display screen; and the processing unit is configured to determine that the first user can view the second display screen if the orientation of the first display screen and/or the orientation of the second display screen change from the initial set of measurements by more than a threshold amount.

20. An apparatus, for controlling the operation of a first electronic device having a first display screen, the apparatus comprising a processing unit that is configured to:

obtain measurements of an orientation of the first display screen, and one or both of a position of the first electronic device relative to a second electronic device, and an orientation of a second display screen of the second electronic device;

determine, using the obtained measurements, whether a user using the second electronic device can view the first display screen; and control the display of information on the first display screen based on whether the user can view the first display screen wherein the processing unit is configured to:

use the orientation of the second display screen and/or position of the first electronic device relative to the second electronic device to estimate a position of the user when using the second electronic device; and determine if the first display screen can be viewed from the estimated position of the user using the orientation of the first display screen.

21. The apparatus as claimed in claim 20, wherein the processing unit is configured to determine whether the user can view the first display screen by:

estimating a position of the user when using the second electronic device using the orientation of the second display screen and/or position of the first electronic device relative to the second electronic device; and using the orientation of the first display screen, the position of the first electronic device relative to a second electronic device and the estimated position of the user to determine if the user can view the first display screen.

22. The apparatus as claimed in claim 20, wherein the processing unit is configured to obtain an initial set of measurements when the first electronic device and the second electronic device are in an arrangement in which the user cannot view the first display screen; and the processing unit is configured to determine that the user can view the first display screen if the orientation of the first display screen and/or the orientation of the second display screen change from the initial set of measurements by more than a threshold amount.

* * * * *